United States Patent
Robertson et al.

(10) Patent No.: US 7,154,401 B2
(45) Date of Patent: Dec. 26, 2006

(54) METHOD AND APPARATUS FOR ASSESSING THE INTEGRITY OF A JEWELLERY SETTING

(75) Inventors: Mark Robertson, Atlantic Highlands, NJ (US); John Humbert, Jr., Morganville, NJ (US)

(73) Assignee: Diamond Alert, LLC., Morganville, NJ (US)

( * ) Notice: Subject to any disclaimer, the term of this patent is extended or adjusted under 35 U.S.C. 154(b) by 237 days.

(21) Appl. No.: 10/508,514

(22) PCT Filed: Apr. 16, 2003

(86) PCT No.: PCT/EP03/03989

§ 371 (c)(1), (2), (4) Date: Sep. 21, 2004

(87) PCT Pub. No.: WO03/089913

PCT Pub. Date: Oct. 30, 2003

(65) Prior Publication Data

US 2005/0141588 A1 Jun. 30, 2005

(30) Foreign Application Priority Data

Apr. 19, 2002 (GB) ................................. 0208942.3

(51) Int. Cl.
*G08B 17/00* (2006.01)

(52) U.S. Cl. .......................... 340/584; 340/999; 29/10; 63/26; 374/45

(58) Field of Classification Search ................. 340/584
See application file for complete search history.

(56) References Cited

U.S. PATENT DOCUMENTS

| 4,163,142 A * | 7/1979 | Descovich et al. ........... 29/705 |
| 4,344,315 A | 8/1982 | Moxon et al. |
| 4,488,821 A | 12/1984 | Wenckus |
| 4,841,543 A | 6/1989 | Dittmar et al. |
| 5,446,595 A * | 8/1995 | McFall ....................... 359/804 |
| 6,265,884 B1 * | 7/2001 | Menashi et al. ............. 324/717 |
| 6,439,766 B1 * | 8/2002 | Nelson ......................... 374/44 |
| 6,928,834 B1 * | 8/2005 | Robertson et al. ............. 63/27 |
| 2002/0034211 A1 | 3/2002 | Baratta |

FOREIGN PATENT DOCUMENTS

DE 34 25 561 A1 1/1985

* cited by examiner

*Primary Examiner*—Daniel Wu
*Assistant Examiner*—Eric M. Blount
(74) *Attorney, Agent, or Firm*—Birch, Stewart, Kolasch & Birch, LLP.

(57) ABSTRACT

There is provided a method for assessing the integrity of grip of a stone in a jewellery setting having plural gripping claws to grip said stone, the method comprising heating the stone; measuring conductive transfer of heat from the stone to each of said plural gripping claws; and comparing said conductive heat transfer to said each gripping claw, wherein a marked difference in conductive heat transfer to any of the gripping claws indicates a lack of integrity of grip. Suitable apparatus is also provided.

41 Claims, 6 Drawing Sheets

METHOD AND APPARATUS FOR ASSESSING THE INTEGRITY OF A JEWELLERY SETTING

TECHNICAL FIELD

The present invention relates to a method and apparatus for assessing whether a precious stone is loose within a jewellery setting.

BACKGROUND TO THE INVENTION

Personal jewellery, such as rings, necklaces, bracelets, etc., are expensive items which can be of great value to their owners. Items of jewellery typically comprise a precious stone in a setting, which itself is typically composed of a precious metal, such as gold, platinum or silver. Both the gemstone and the setting may be extremely expensive individually, but the combination may be crafted together by a skilled smith to produce a work of extreme value. Furthermore, as items of jewellery are often given as gifts to commemorate special occasions, such as birthdays, anniversaries, engagements and weddings, they are frequently of significant sentimental value to the wearer.

A common problem experienced by wearers and owners of items of jewellery is that the precious gem stone-becomes loose in its setting and may become dislodged. This may occur due to the age of the jewellery or if it is subjected to a jolt or shock, for example if a ring falls from the wearer's finger onto the ground. Typically the gem stone will 'work loose' over an extended period of time, following such a jolt or shock. The wearer of the jewellery is generally unaware that the precious stone has become dislodged from its setting and consequently doesn't realise that there is a problem. Unfortunately the result all too often is that the precious stone eventually works free of the setting and is lost, causing both financial and often personal loss for the wearer. Although the owner may replace the stone (often at significant expense) with a similar gem, the stone may have held significant sentimental value and consequently can never truly be replaced.

The present invention addresses the problem of assessing whether a precious stone has become loose or dislodged from its jewellery setting. In particular, it provides a means for assessing whether the integrity of grip of a stone is intact in a jewellery setting having plural gripping claws to grip said stone. The method relies on measuring heat transfer (i.e. conductivity of heat) from the stone to the gripping claws. Good heat transfer will be expected for good claw integrity, whereas poor heat transfer provides an indication that the stone has come loose from the claw, and hence is loose in the overall setting.

The method is relatively straightforward to implement at low cost, and is non-invasive. That is to say, it may be conducted without manual prodding or tinkering with the setting, which may in itself result in damage if not conducted with great care.

The method also provides the advantage that it may be used to identify a single poor stone-claw gripping relationship, even in a jewellery setting (e.g. a ring) where the overall integrity (as a result of all the other claw grips) is acceptable. It therefore provides a way of pre-emptively predicting total (i.e. catastrophic) failure setting integrity before it happens.

SUMMARY OF INVENTION

According to one aspect of the present invention, there is provided a method for assessing the integrity of grip of a stone in a jewellery setting having plural gripping claws to grip said stone, the method comprising heating the stone; measuring conductive transfer of heat from the stone to each of said plural gripping claws; and comparing said conductive heat transfer to said each gripping claw, wherein a marked difference in conductive heat transfer to any of the gripping claws indicates a lack of integrity of grip.

Suitably, the method additionally comprises identifying which of the gripping claws has said marked difference in conductive heat transfer, thereby indicating lack of integrity of grip of any particular gripping claw (i.e. the gripping claw which displays the marked difference).

The invention provides a method for assessing the integrity of grip of a stone in a jewellery setting having plural gripping claws to grip said stone. Such settings are familiar components of items of jewellery such as rings, necklaces, bracelets, brooches, earrings, tiepins, cuff links, necklaces and pendants. Other mountings and/or settings may also be present.

The setting has plural gripping claws (e.g. prong-like, gripping arms) to grip the stone therein. The claws are generally comprised of a metal, generally a precious metal such as gold, silver or platinum. The number of claws will vary depending on the setting type, but in general from four to eight, often six, claws are present.

Suitably, the stone is a precious stone selected from the group consisting of diamond, sapphire, pearl, ruby, amethyst, topaz, garnet, aquamarine, emerald, peridot, opal and turquoise. Diamonds are particularly, envisaged.

It will be appreciated that both the claws and the stone are generally, comprised of materials having good heat transfer properties (i.e. good heat conductivity). The heat transfer property of metals needs no further explanation, and that of precious stones such as diamonds is also well documented. It will also be appreciated that the present invention relies on these heat transfer properties, and in particular on the different heat transfer properties of the stone compared to the material of the claws.

The method comprises a step involving heating the stone. All suitable methods of heating are envisaged, particularly direct contact heating (e.g. by bringing a heater into contact with the stone). It will be appreciated that, in the context of the present invention, the method of heating should be isolated, as much as possible, from the gripping claws (e.g. by locating the heater distant from the claws and/or in some way providing a physical isolation, for example, a heat screen, between it and the claws).

Typically, the heating is conducted for a matter of seconds, say one to ten seconds, although this may be varied dependent on the particular stone and claw materials.

The method also comprises a step involving measuring the conductive transfer of heat from the stone to each of said plural gripping claws. Again, various measurement or detection methods are envisaged.

In one particular embodiment, the temperature of each gripping claw is measured. A rise in temperature is thus, used to indicate heat transfer. The temperature may be measured by any suitable thermometer, including an electro, thermometer. Examples of suitable electro thermometric methods include the use of resistance thermometry, thermocouples, thermopiles, bolometers and semiconductor devices. Bolometers record thermal radiation, as opposed to conductive heat transfer. In another embodiment, heat transfer to each gripping claw is measured visually, for example using an infrared camera.

The method further involves the step of comparing the conductive heat transfer to said each gripping claw. What is typically envisaged is a mutual, cross-comparison of conductive heat transfer between the respective gripping claws. In one example, respective temperature measurements relevant to each claw are compared. In another, the relative visual characteristics are compared using the display from an infrared camera.

A marked difference in conductive heat transfer to any of the gripping claws is used in the method herein to indicate a lack of integrity of grip. It will be appreciated that heat transfer from a stone which is tightly gripped by any particular claw to that particular claw will be greater than if the claw only loosely grips the stone (i.e. where the stone has become loose in that clawed part of the setting).

What constitutes a marked difference herein will be apparent to one skilled in the art. In plain terms, it goes beyond the sort of difference which might reasonably be expected from claw to claw given normal (e.g. manufacturing-derived) tolerances of the setting. The detection of the marked difference may employ any suitable means, particularly those employing some sort of electronic processing capability relying on various mathematical algorithms. Suitable (e.g. statistical) methods are well known in the art.

The marked difference may be signalled such as to indicate a lack of integrity for the setting as a whole (i.e. one loose claw indicates a setting of unacceptable integrity).

In one preferred aspect however, the method additionally comprises indicating which of the gripping claws has said marked difference in conductive heat transfer, thereby indicating lack of integrity of grip of one or more particular gripping claws. The method may also therefore be used as a diagnostic to indicate which claw or claws should be made the subject of a repair operation.

In another preferred aspect, the method additionally comprises providing an alert when either a marked difference or absence thereof in conductive heat transfer is detected (i.e. negative or positive integrity alert). Thus, the method acts such as to alert a user that a stone is loose within the jewellery setting. The alert is for example, provided by emitting energy in a form selected from the group consisting of electro-magnetic radiation, sound, electrical, kinetic and thermal energy. Preferably, an alerting light signal is emitted.

In a development of the alert principle, the intensity of an alerting signal is coupled to the amount of heat transfer detected. Thus, in one example, a strong light signal may be used to indicate good heat transfer to a particular claw and hence, good claw-stone contact integrity, whereas a weaker light signal indicates weaker contact and poorer integrity.

In embodiments, the alert may be arranged to indicate the integrity of the setting as a whole, or a claw-by-claw alerting system may be envisaged. In an example of the latter system, a six-claw setting is coupled to a corresponding six light alert display.

According to one aspect of the present invention, there is provided an apparatus for conducting the method herein. That is to say, apparatus for use in assessing the integrity of grip of a stone in a jewellery setting having plural gripping claws to grip said stone.

Suitably, the apparatus comprises a holder for holding said jewellery setting; a heater for heating the stone; and a heat transfer measure for measuring conductive transfer of heat from the stone to each of said plural gripping claws, wherein a marked difference in conductive heat transfer to any of the gripping claws indicates a lack of integrity of grip.

Optionally, the apparatus comprises a comparator for comparing said conductive heat transfer to said each gripping claw. Alternatively, such comparison may be conducted manually, for example by a user comparing the measurement output of the heat transfer measure.

Optionally, the apparatus enables the identification of which of the gripping claws has the marked difference in conductive heat transfer, thereby indicating lack of integrity of grip of any particular gripping claw (i.e. the gripping claw which displays the marked difference).

The apparatus provides a method for assessing the integrity of grip of a stone in a jewellery setting having plural gripping claws to grip said stone. Such settings are familiar components of items of jewellery such as rings, necklaces, bracelets, brooches, earrings, tiepins, cuff links, necklaces and pendants. Other mountings and/or settings may also be present.

The setting has plural gripping claws (e.g. prong-like, gripping arms) to grip the stone therein. The claws are generally comprised of a metal, generally a precious metal such as gold, silver or platinum. The number of claws will vary depending on the setting type, but in general from four to eight, often six, claws are present.

Suitably, the stone is a precious stone selected from the group consisting of diamond, sapphire, pearl, ruby, amethyst, topaz, garnet, aquamarine, emerald, peridot, opal and turquoise. Diamonds are particularly, envisaged.

It will be appreciated that both the claws and the stone are generally, comprised of materials having good heat transfer properties (i.e. good heat conductivity). The heat transfer property of metals needs no further explanation, and that of precious stones such as diamonds is also well documented. It will also be appreciated that the present invention relies on these heat transfer properties, and in particular on the different heat transfer properties of the stone compared to the material of the claws.

The apparatus comprises a holder for holding the jewellery setting. Various configurations are envisaged, including those in which the holder holds the setting directly, and those in which another part of the item of jewellery is held. In one particular, example the item of jewellery is a ring having a stone setting and the holder holds the spur (i.e. finger-receiving part) of the ring. In one aspect, the holder comprises a spring-loaded holder for part of the jewellery item.

The apparatus comprises a heater for heating the stone. All suitable heaters are envisaged, particularly direct contact heaters (i.e. those that contact the stone and provide heat by direct conductive transfer thereto). It will be appreciated that the heater should be isolated, as much as possible, from the gripping claws. Thus, in aspects, the heater is located distant from the claws. In other aspects, the heater is physical isolated from the claws, for example, by providing a heat screen (e.g. a ceramic) between it and the claws.

The heater may be located at a fixed point in the apparatus. In one aspect however, the heater is mounted for movement within the apparatus such that it is moveable from a non-contact position, in which it is not in heating contact with the stone to a contact position, in which it contacts the stone for heating thereof. The mounting may have any suitable form including spring-loaded mountings.

Typically, the heating is conducted for a matter of seconds, say one to ten seconds, although this may be varied dependent on the particular stone and claw materials. The heating may be continuous or it may be pulsed.

The apparatus also comprises a heat transfer measure for measuring conductive transfer of heat from the stone to each of said plural gripping claws. Again, various heat transfer measurement or detection apparatus or devices are envisaged.

In one particular embodiment, the heat transfer measure comprises a temperature sensor (e.g. a thermistor or RTD) to measure the temperature of each gripping claw. A rise in temperature of the gripping claw indicates heat transfer. Any suitable thermometer may be used, including an electro thermometer. Examples of suitable electro thermometers include resistance thermometers, thermocouples, thermopiles, bolometers and semiconductor devices. Bolometers record thermal radiation, as opposed to conductive heat transfer. Electro thermometers have the advantage that heat transfer data is captured in digital form, and that data may thus, be transferred to other electronic data handling equipment for analysis, display and storage.

In another embodiment, the heat transfer measure comprises a visual measure such as an infrared detector (e.g. an infra-red camera).

In one aspect, the heat transfer measure comprises plural temperature sensors, each of which is mounted to a sensor mounting. Preferably, the sensor mounting is a common for all of the sensors (i.e. one single mounting for all sensors). Suitably, the sensors are mounted such that in use, when the sensor mounting is brought proximal to the jewellery item each sensor locates adjacent to, or in a preferred aspect contacts, a gripping claw of the jewellery item.

In one aspect, the sensor mounting has a generally concave surface (e.g. umbrella-shaped form) and comprises plural temperature sensors spaced at regular intervals (e.g. equidistantly spaced on the periphery thereof).

The sensor mounting may be located at a fixed point in the apparatus. In one aspect however, the sensor mounting is mounted for movement within the apparatus such that it is moveable from a non-contact position, in which the temperature sensors thereof are distant from the gripping claws of the jewellery setting to a contact position, in which in which the temperature sensors thereof contact the gripping claws of the jewellery setting. The sensor mounting may have any suitable form including a spring-loaded mounting.

Use of the apparatus in the method herein involves making a comparison of the conductive heat transfer to each gripping claw. What is typically envisaged is a mutual, cross-comparison of conductive heat transfer between the respective gripping claws. In one example, respective temperature measurements relevant to each claw are compared. In another, the relative visual characteristics are compared using the display from an infrared camera.

The comparison may be conducted manually by the user. Optionally, the apparatus may comprise a comparator for comparing the conductive heat transfer to each gripping claw. The comparator, may for example, comprise an electronic data processor for processing heat transfer measurement data.

A marked difference in conductive heat transfer to any of the gripping claws is used in the method herein to indicate a lack of integrity of grip. The comparator herein, may employ any suitable means for determining the presence of a marked difference. In particular, the comparator may utilise electronic processing capability e.g. making use of mathematical algorithms to make the comparative analysis. Suitable (e.g. statistical) methods are well known in the art.

In one aspect, the apparatus includes an indicator to indicate the presence of a marked difference, and thus to indicate a lack of integrity for the setting (e.g. one loose claw indicates a setting of unacceptable integrity as a whole).

In another aspect, the apparatus includes an indicator for indicating which of the gripping claws has said marked difference in conductive heat transfer, thereby indicating lack of integrity of grip of one or more particular gripping claws. The apparatus may also therefore be used diagnostically to indicate which claw or claws should be made the subject of a repair operation.

In another aspect, the apparatus additionally comprises an alert for alerting when either a marked difference or absence thereof in conductive heat transfer is detected (i.e. negative or positive integrity alert). Thus, the apparatus acts such as to alert a user that a stone is loose within the jewellery setting.

The alert is for example, provided by emitting energy in a form selected from the group consisting of electromagnetic radiation, sound, electrical, kinetic and thermal energy. Preferably, an alerting light signal is emitted. The alert may for example, involve emitting light or sound energy continuously or intermittently. Suitably, alert comprises a light emitting diode. More preferably, the emitter emits coloured light.

In a development of the alert principle, the intensity of an alerting signal is coupled to the amount of heat transfer detected. Thus, in one example, a strong light signal is used to indicate good heat transfer to a particular claw and hence, good claw-stone contact integrity, whereas a weaker light signal indicates weaker contact and poorer integrity.

In embodiments, the alert may be arranged to indicate the integrity of the setting as a whole, or a claw-by-claw alerting system may be envisaged. In an example of the latter system, a six-claw setting is coupled to a corresponding six light alert display.

Suitably, the apparatus additionally comprises a power source for powering any electrical components thereof. Suitably, the power source is selected from the group consisting of battery (e.g. a lithium battery), fuel cell and solar cell.

According to a particular aspect of the present invention, an apparatus for use in assessing the integrity of grip of a stone in a jewellery setting of a ring, said jewellery setting having plural gripping claws to grip said stone, the apparatus comprising a holder for holding said ring; a heater for heating the stone; and a heat transfer measure for measuring conductive transfer of heat from the stone to each of said plural gripping claws, wherein a marked difference in conductive heat transfer to any of the gripping claws indicates a lack of integrity of grip.

Suitably, the apparatus is configured in the form of a box with a lid (e.g. hinged). The holder for the ring comprises a well defined within the box; the heater is a contact heater located on the lid of the box; and the heat transfer measure comprises multiple temperature probes located within the box to contact the gripping claws when the holder receives the ring. The box is configured such that the heater only contacts the stone when the lid of the box is closed. The box is also provided with various indicators (e.g. LEDs) for indicating the integrity of the stone setting.

Whilst, the present invention has been described in terms of a method and apparatus relying on measure of heat transfer to indicate lack of setting integrity, it may be appreciated that other flow characteristics could also be employed as an alternative or complementary method. Thus, for example electrical current flow may also be assessed.

BRIEF DESCRIPTION OF DRAWINGS

Preferred embodiments of the present invention will now be described with reference to the accompanying drawings in which:

FIG. 2b is a sectional top view of the second apparatus of FIG. 2a;

DETAILED DESCRIPTION OF THE DRAWINGS

Figure 1:
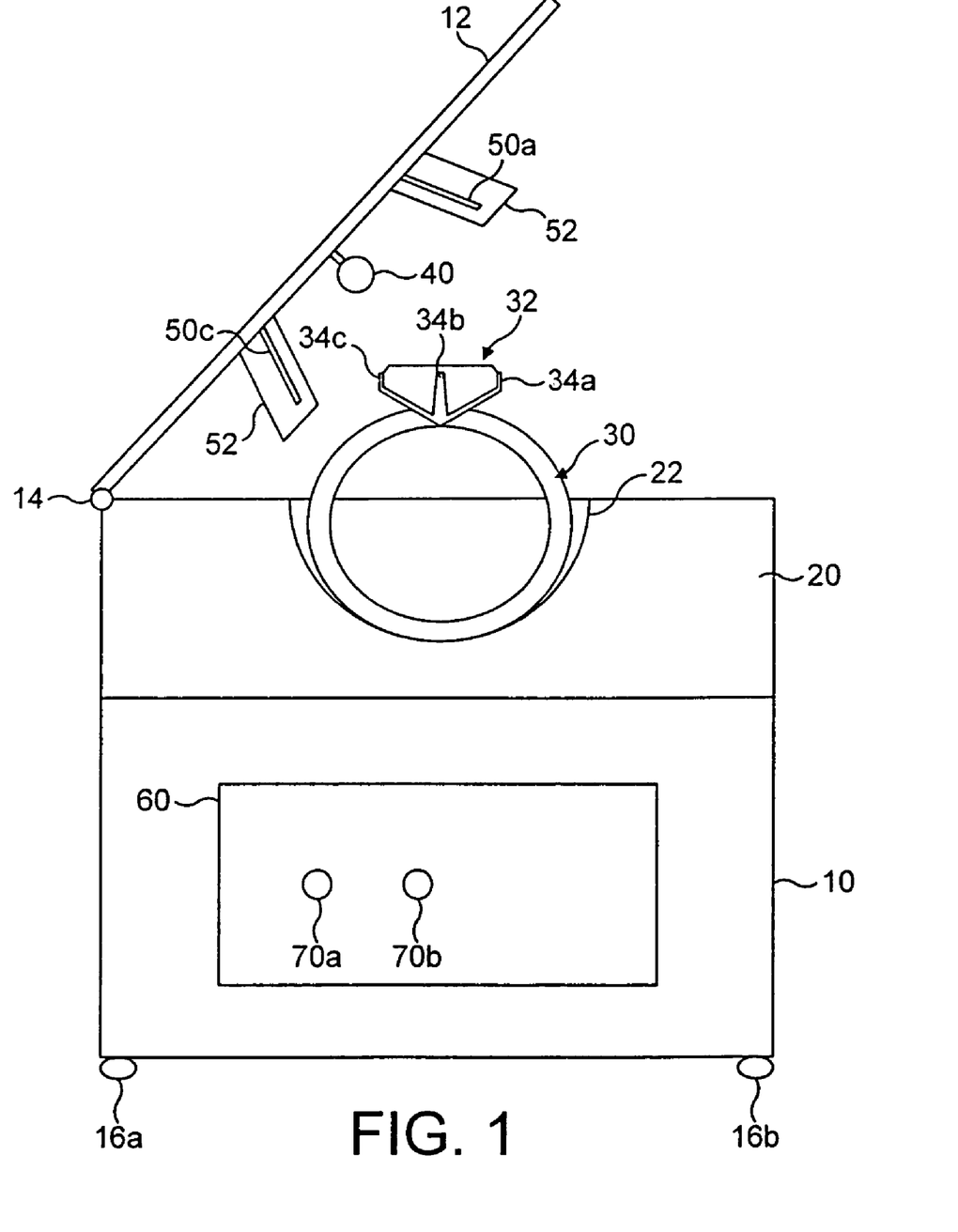
FIG. 1 is a sectional side view of an apparatus for use in accord with the present invention.

FIG. 1 shows desk top apparatus herein, in the form of a box housing 10 having a lid 12 mounted on a hinge mounting 14. The housing 10 is itself mounted on feet 16a, 16b. The interior of the housing 10 includes cushioning 20 having a cutaway well depression 22 shaped for snug receipt of the spur of a dress ring 30 having a diamond 32 mounted in a setting comprising plural gripping claws 34a–c. Heater 40 is mounted on the inside of the lid 12. On either side of the heater 40, there are further mounted electro thermometric temperature probes 50a, 50c. Each probe 50a, 50c is thermally insulated from both the heater 40 and from the other probes 50a, 50c by a conically shaped ceramic heat screen 52. In embodiments, the conical heat screen 52 and probes 50a, 50c are supplied as a replaceable sub-assembly, and the lid is designed to accommodate such sub-assemblies of varying size such that different ring 30 shapes and configurations (e.g. four claw, six claw etc.) may be assessed.

In use, the lid 12 of the box 10 is closed and the heater 40 directly contacts the diamond 32. Each temperature probe 50a, 50c respectively contacts a claw 34a, 34c to enable the measurement of the temperature of each claw 34a-c separately as heat is applied to the diamond 32. The temperature probes communicate with circuitry 60 (shown schematically) to.

The method of use is as follows: Once the ring 30 has been suitably placed in the apparatus, the lid 12 of the box 10 is closed. Power is then applied to the heater 40, which heats up the diamond 32. That heat conducts through the diamond 32 and potentially to the claws 34a–c of the setting. The degree of heat transfer is measured by reference to the temperature recorded by each respective temperature probe 50a, 50c. If the diamond-claw contact is good (i.e. positive grip integrity) the heat transfer to the claw 34a–c will also be good, and the temperature measured at the claw 34a–c will increase rapidly. If however, the diamond-claw contact is poor (i.e. negative grip integrity) the heat transfer to the claw 34a–c will also be poor, and the temperature of the claw 34a–c will not increase rapidly. The measured temperature values will be communicated to the circuitry 60, and may simply be displayed on a display or may be subject to comparative analysis to identify any marked difference in heat transfer, and thereby grip integrity of each claw 34a–c and of the setting as a whole. LED emitters 70a, 70b are used to display alerting signals relating to grip integrity of the setting.

Figure 2A:
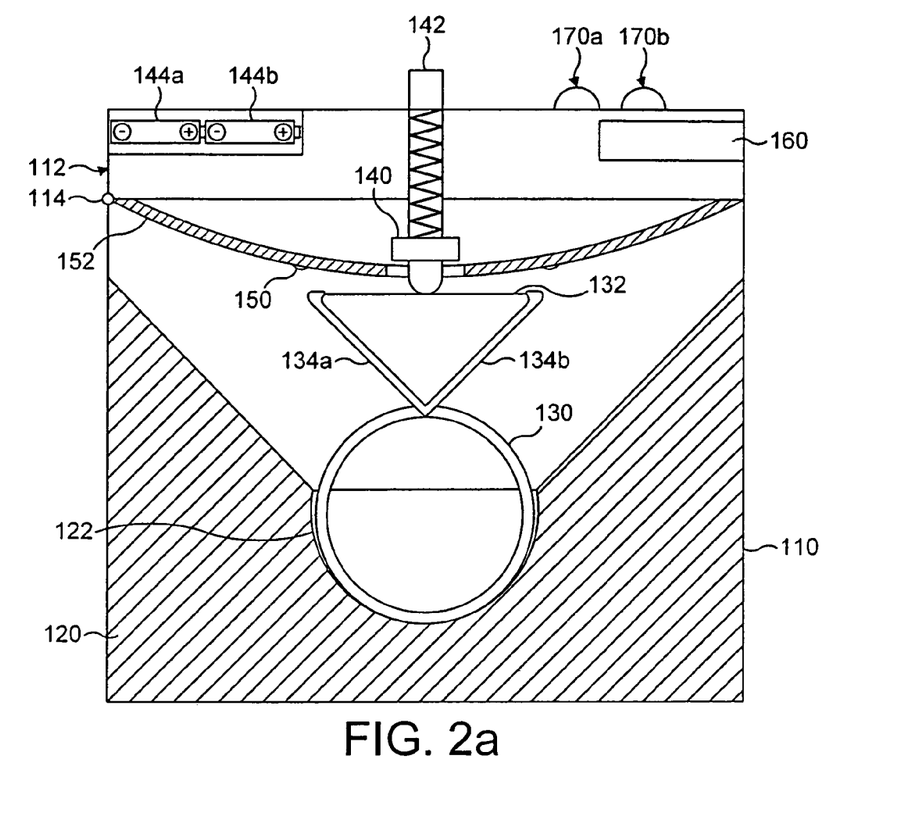
FIG. 2a is a sectional side view of a second apparatus for use in accord with the present invention.
Figure 2B:
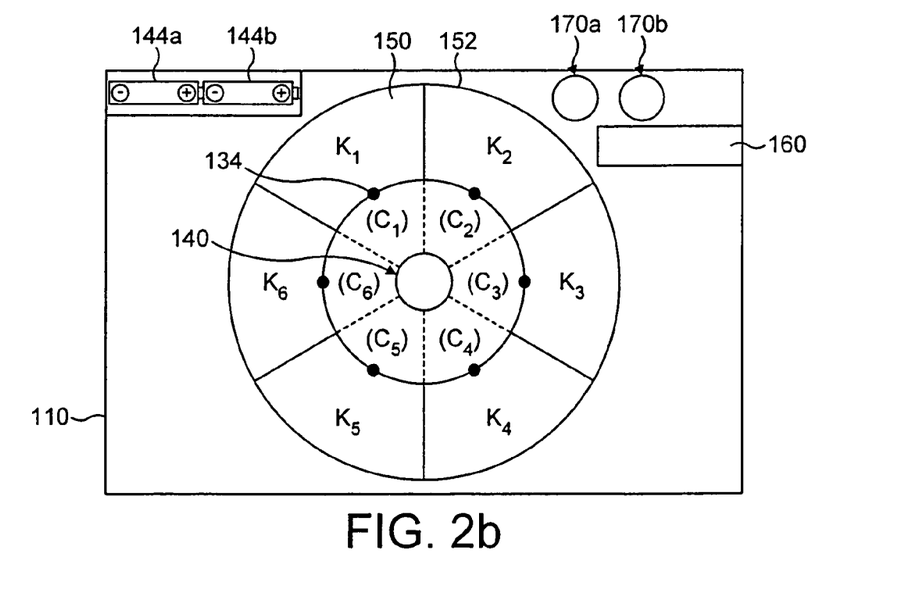

FIGS. 2a and 2b show a further desk top apparatus herein, in the form of a box housing 110 having a lid 112 mounted on a hinge mounting 114. The interior of the housing 110 includes heat-resistant foam cushioning 120 having a cutaway well depression 122 shaped for snug receipt of the spur of a dress ring 130 having a diamond 132 mounted in a setting comprising plural gripping claws ($C_1$–$C_6$ of FIG. 2b) 134a, 134b (two only shown for clarity in FIG. 2a). Heater 140, operable in response to push button 142 and powered by batteries 144a, 144b, is mounted on the inside of the lid 112.

The lid 112 is further provided with a concave insert 152, which is formed of ceramic, and has temperature sensors 150 ($K_1$–$K_6$ of FIG. 2b) spaced at regular intervals therein. In embodiments, the concave insert and sensors 150 are supplied as a replaceable sub-assembly, and the lid is designed to accommodate such sub-assemblies of varying size such that different ring 130 shapes and configurations (e.g. four claw, six claw etc.) may be assessed.

In use, the lid 112 of the box 110 is closed and the heater 140 directly contacts the diamond 132. Each temperature sensor 50 ($K_1$–$K_6$ of FIG. 2b) separately measures the temperature of a respective claw 134a, 34c ($C_1$–$C_6$ of FIG. 2b). The temperature measurements are communicated to circuitry 160 (shown schematically) which in turn communicates with green 170a and red 170b LEDs.

The method of use is as follows: Once the ring 130 has been suitably received in the holder 122, the lid 112 of the box 110 is closed. The button 142 is pressed and power is applied to the heater 140, which in turn heats the diamond 132. The heat conducts through the diamond 132. The degree of heat transfer to the claws 134a, 134c ($C_1$–$C_6$ of FIG. 2b) is measured by reference to the temperature recorded by each respective temperature sensor 150 ($K_1$–$K_6$ of FIG. 2b). If the diamond-claw contact is good (i.e. positive grip integrity) the heat transfer will also be good, and the temperature measured at the claw 134a, 134c ($C_1$–$C_6$ of FIG. 2b) will increase rapidly. If however, the diamond-claw contact is poor (i.e. negative grip integrity) the heat transfer will also be poor, and the temperature of the claw 134a, 134c ($C_1$–$C_6$ of FIG. 2b) will not increase rapidly. The measured temperature values are communicated to the circuitry 160 and subjected to comparative analysis to identify any marked differences in heat transfer, and hence the grip integrity of the setting as a whole. If acceptable setting integrity is found (i.e. no marked difference in heat transfer) the green LED emitter 170a lights up. If however, unacceptable setting integrity is found (i.e. a marked difference in heat transfer between the claws) the red LED emitter 170b lights up.

Figure 3:
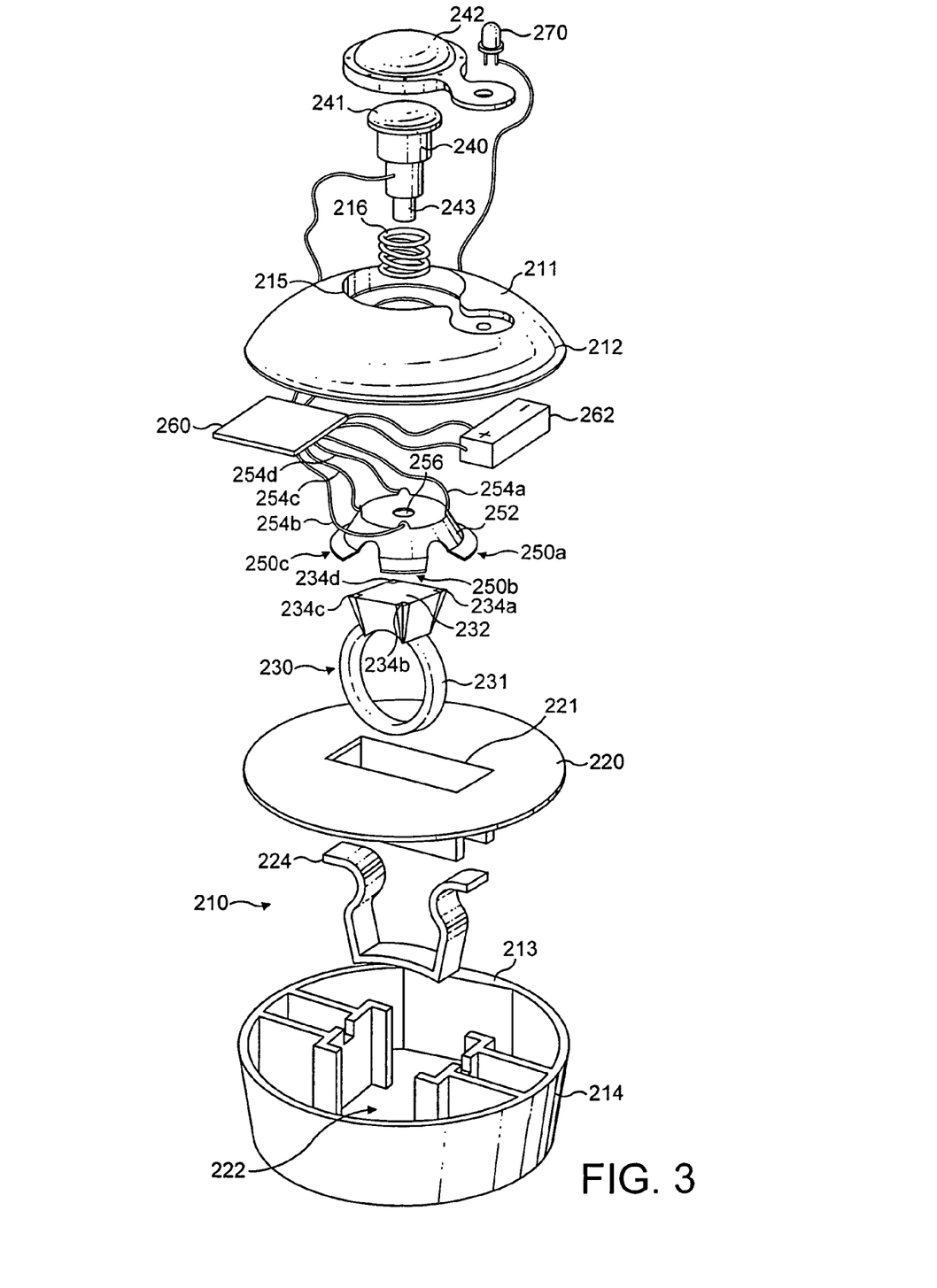
FIG. 3 is an exploded perspective view of a third apparatus for use in accord with the present invention.

FIG. 3 shows a compact apparatus herein, in the form of a casing 210 having respective top 212 and base 214 moulded parts, which in use are hinge mounted at respective hinge mounting points 211 and 213. The base 214 of the casing 210 is provided with moulded cover 220, which is itself provided with rectangular access port 221 to allow access to ring-receiving cavity 222 of the base 214. The cavity 222 is shaped for snug receipt of the spur 231 of a dress ring 230. Once received, the spur 231 is gripped by spring-loaded ring holder 224, which also locates in the cavity 222. The ring 230 has a precious stone (e.g. a diamond) 232 mounted in a stone setting comprising plural gripping claws 234a–c formed of precious metal (e.g. gold).

Cylindrical plug-shaped heater 240 is spring-mounted within the top moulded part 212, which receives both the heater 240 and spring 216 in access hole 215 provided therein. Moulded cap 242 is provided to the head 241 of the heater 240 such that downward pressure applied to the cap 242 results in the heater 240 being pushed generally against the spring 216 and towards the interior of the casing 210.

Umbrella-shaped sensor diaphragm 252 locates between the top moulding 212 and the cover 220 such that in use, it contacts the received ring 230. The diaphragm 252 has central aperture 256, through which the tail 243 end of the heater 240 may protrude in use, once the heater 240 is pushed into the casing 210. The tail end 243 of the heater 240 thereby contacts the stone 232 of the ring 230 to enable heating thereof.

Figure 3A:
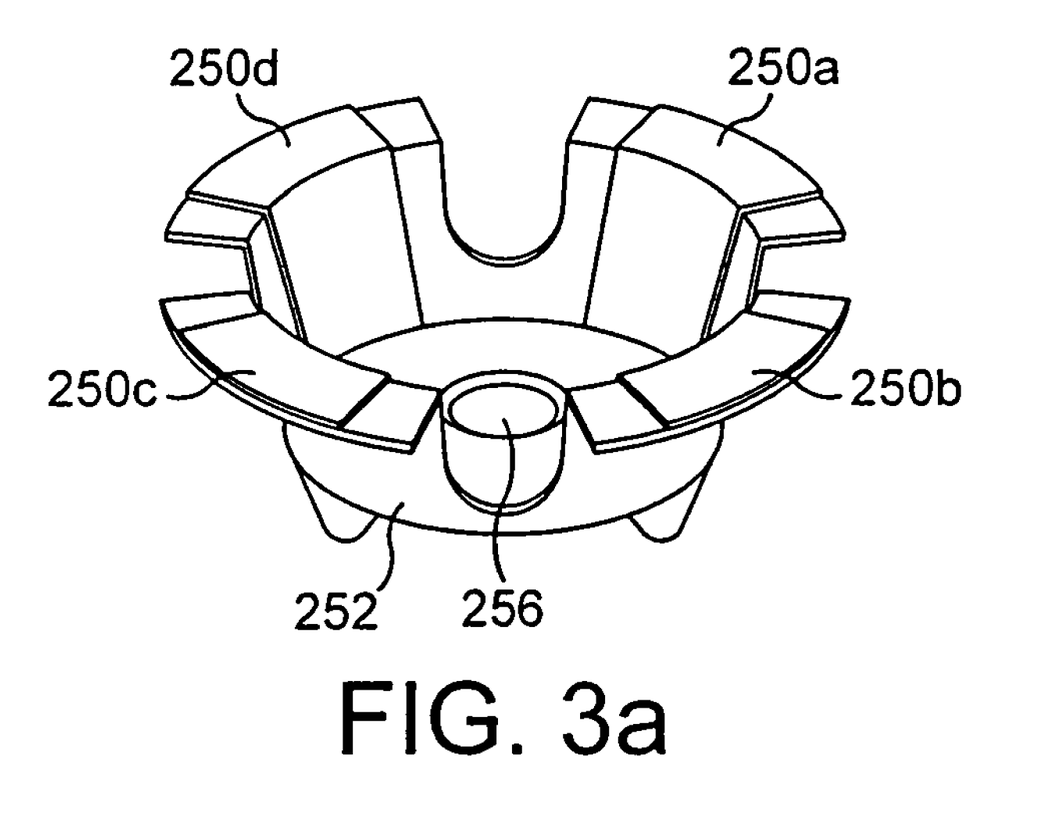
FIG. 3a is a perspective detail view of the underside of a sensor diaphragm, which forms part of the apparatus shown in FIG. 3.

Having regard also to FIG. 3a, it may be seen that the concave underside of the sensor diaphragm 252 is provided with four equidistantly spaced electro thermometric temperature probes 250a–d. Each probe 250a–d is thermally insulated from both the heater 240 and from the other probes 250a–d. Each probe 250a–d connects via separate connector wire 254a–d to printed circuit board 260. It will be seen that the circuit board 260 is also wired to battery 262; heater 240; and LED emitter 270. The circuit board 260 enables control of all elements to which it is wired up.

In embodiments, the sensor diaphragm 252 and temperature probes 250a–d are supplied as a replaceable sub-assembly, and the top 212 of the casing 210 is designed to accommodate sub-assemblies of varying size such that different jewellery item 230 shapes and configurations (e.g. four claw, six claw etc.) may be assessed.

In use, the casing 210 is closed and when the heater 240 is pushed into the casing 210, the tail end 243 thereof directly contacts the diamond 232. Each temperature probe 250a–d respectively contacts a claw 234a–d of the ring 230 to enable the measurement of the temperature of each claw 234a–d separately as heat is applied to the diamond 232. The temperature probes 250a–d communicate with the circuit board 260 to assess any differences in heat transfer to each respective claw 234a–d.

The method of use is as follows: The ring 230 is placed in the receiving cavity 222 such that it is retained by spring-loaded ring holder 224. The top 212 and base 214 parts of the casing are then brought into mating contact, thereby also bringing the probes 250a–d of the sensor diaphragm 252 into contact with the respective gripping claws 234a–d of the ring 230. The moulded cap 242 is depressed thereby bringing the tail end 243 of the heater 240 into contact with the stone 232. Power is then applied to the heater 240, which heats up the stone 232. That heat conducts through the diamond 232 and potentially to each claws 234a–d of the setting 230. The degree of heat transfer is measured by reference to the temperature recorded by each respective temperature probe 250a–d. If the diamond-claw contact is good (i.e. positive grip integrity) the heat transfer to the claw 234a–d will also be good, and the temperature measured at the claw 234a–d will increase rapidly. If however, the diamond-claw contact is poor (i.e. negative grip integrity) the heat transfer to the claw 234a–d will also be poor, and the temperature of the claw 234a–d will not increase rapidly. The measured temperature values will be communicated to the printed circuit board 260, and may simply be displayed on a display (not visible) or may be subject to comparative analysis to identify any marked difference in heat transfer, and thereby grip integrity of each claw 234a–d and of the setting as a whole. LED emitter 270 is used to display an alerting signal relating to indicate either positive or negative grip integrity of the setting.

Figure 4:
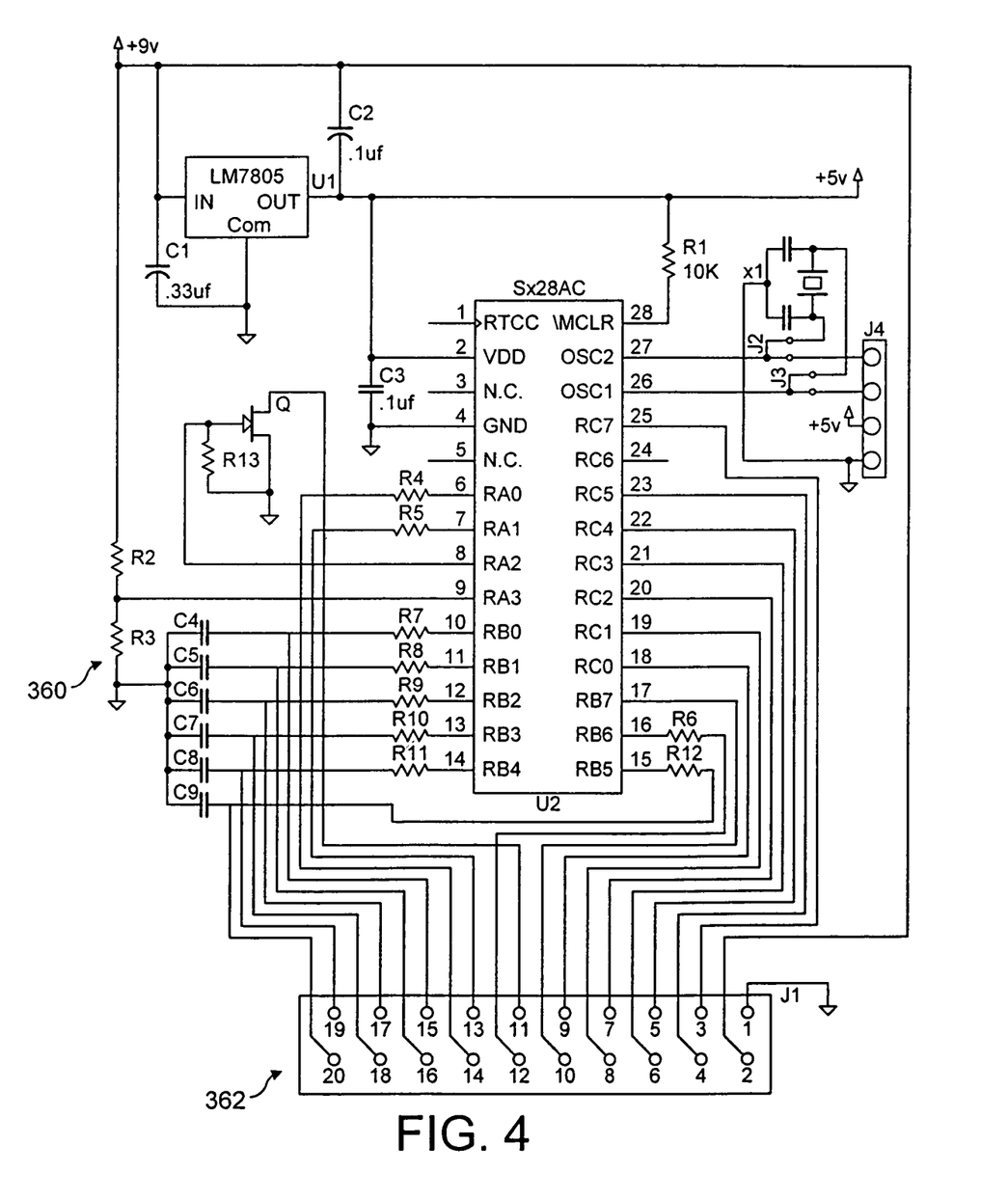
FIG. 4 shows a circuit diagram of a circuit suitable for use with apparatus herein.

FIG. 4 illustrates the layout of a suitable circuit 360 for suitable for use with apparatus herein (e.g. as shown in the previous figures).

The circuit 360 comprises plural connector pin inputs 362, which correspond to inputs as follows:

| Pin | Function |
| --- | --- |
| Pin 1: | Ground |
| Pin 2: | 9 volt battery input |
| Pin 3: | 19.2K baud serial out test |
| Pin 4: | Start button |
| Pins 5–10: | Continuity connections |
| Pin 11: | Heater input |
| Pin 12: | Power LED |
| Pins 13–14: | Status LED |
| Pins 15–20: | Temperature sensor inputs (e.g. 10K Ohm thermistor sensors) |

The other components of the circuit correspond to:

| Ref | Description |
| --- | --- |
| R1 | Resistor: ⅛ watt 10K Ohms |
| R2 | Resistor: ⅛ watt 68K Ohms |
| R3 | Resistor: ⅛ watt 47K Ohms |
| R4–R6 | Resistor: ⅛ watt 470 Ohms |
| R7–R12 | Resistor: ⅛ watt 51 Ohms |
| R13 | Resistor: ⅛ watt 1 M Ohms |
| C1 | Capacitor 0.33 microfarad electrolytic 50 volts |
| C2 | Capacitor 0.1 microfarad electrolytic 50 volts |
| C3–C9 | Capacitors 0.1 microfarad ceramic disk or surface mount |
| X1 | Ceramic resonator Murata 50 MHz |
| U1 | 5 Volt regulator, LM7805 |
| U2 | Ubicom SX28AC |
| J1 | 20 pin ribbon connector |
| J2–J3 | 2 pin jumper |
| J4 | 4 pin jumper block |
| Q1 | Power MOSFET IRF510 |

It will be appreciated that the circuit of FIG. 4 is suitable for use with apparatus incorporating six temperature sensors (each feeding into one of Pins 15–20 respectively) and that variations including a smaller greater number of temperature sensor inputs are possible.

Figure 5:
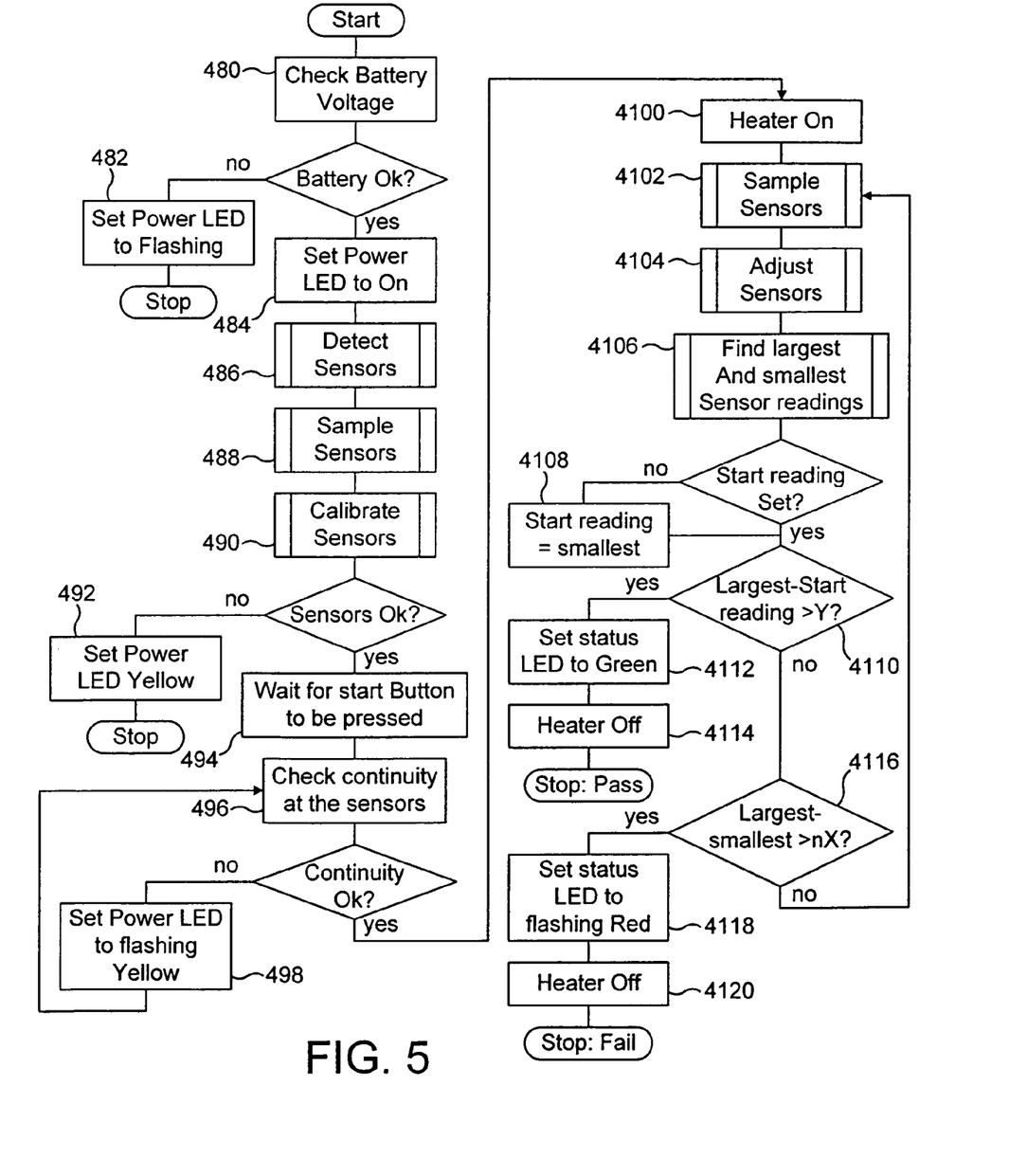
FIG. 5 is a flow chart illustrating the mode of operation of an apparatus herein.

FIG. 5 illustrates in flowchart form the operation of suitable apparatus herein (e.g. of the general type as previously described in detail with reference to FIGS. 1 to 4). As illustrated, the operation comprises a set of steps for initialisation of the apparatus (shown on the left hand side of the diagram) and a set of steps for testing the integrity of an item of jewellery (shown on the right hand side of the diagram). It will be appreciated that the operations will typically occur under the control of the control electronics (e.g. of the PCB 260 of FIG. 3 or as shown in FIG. 4). The operations occur once an item of jewellery has been received by the apparatus.

Referring now to FIG. 5. Once the apparatus is turned on, an initial check 480 is made on the battery. If the battery is insufficiently charged up, a warning 482 is given by way of a flashing LED. If the battery is fine, a 'normal power' LED light is illuminated 484. A series of checks 486, 488, 490 are then made on the individual temperature sensors.

First, a simple check 486 is made to detect the sensors. The purpose of this initial check 486 is simply to check that the sensors are active and are in communication with the control electronics.

Secondly, an initial set of temperature readings 488 is taken from each sensor and these are cross-compared to establish an estimate of the noise arising from routine variation between the sensors. In more detail, the cross-comparison made is between each pair of sensors so that for example if there are three sensors A, B and C three cross comparisons will be made corresponding to AB, AC and BC combinations. The cross-comparison samplings are repeated until a reliable average value for each sensor is obtained based on a good estimate for the background variation.

Finally, the sensors are cross-calibrated 490 by reference to the initial readings from each and detected differences. The highest and lowest detected initial readings (from any sensor) are stored for future reference. It will be appreciated that in general terms, the difference (X) between such highest and lowest readings define a 'largest, normally observed difference' value, which arises for background noise/apparatus constraint reasons. A 'greater than normal difference' value may thus also be defined to be for example, >nX, where n is a number greater than 1. It will be appreciated that if during a ring test operation, an 'recorded difference'>nX is recorded this indicates that one or more sensors is recording an abnormal temperature (compared to the others) which in turn, indicates poor gripping integrity for the claw associated with that one or more particular sensors.

If the three initial checks 484, 486, 488 are successful, the apparatus will go into wait mode 494 in preparation for activation of the jewellery test procedure. Any problem is indicated by an LED 492 showing yellow status. In the wait mode, the continuity of the sensors is continually checked 496 and again, any problem is shown by an LED signal 498.

Moving to the right hand side of the flow chart, in a jewellery test operation the heater is turned on 4100 such that (as previously described in earlier parts of the present description) heat is transferred directly to the stone and indirectly to the gripping claws of its mounting and to the temperature sensors of the apparatus associated with each claw. During the heating operation, the temperature sensors are continually sampled 4102 to provide individual temperature sensor readings.

The sampled temperature readings are then cross-compared 4104 to estimate the variation between the readings observed for each sensor. The method of cross-comparison is pair-wise, as previously described in relation to the initial cross-comparisons 488, 490. The largest and smallest readings for each sampling are stored 4106.

The heating operation is continued until a pre-defined (temperature sensor) reading rise (Y) is detected by at least one sensor. An initial start reading is set 4108 by reference to the lowest sensor reading obtained (during the initialisation operation). As the heating operation proceeds, the largest reading recorded for any sensor is subtracted 4110 from that start reading and when the subtracted value exceeds Y, the heating operation is turned off 4114 as indicated by a green LED 4112.

Throughout, the heating operation and at each sampling point a comparison 4116 is established between the highest reading recorded at any sensor and the lowest reading recorded at any sensor. If the difference between any lowest and highest reading is >nX (as set previously) this indicates uneven heat flow to one of the sensors, which in turn indicates poor grip integrity of the relevant claw. In this case, a red flashing LED status light is illuminated 4118 to indicate 'fail test' and the heater is switched off 4120. If however, no such >nX difference is recorded, the heating operation is continued throughout its normal course until the maximum reading rise Y value is exceeded 4110, 4112, 4114.

An illustrative set of readings is now given for an apparatus having four sensors used to test two different four clawed jewellery item. In each case, the Y value is defined at 200. That is to say, once a sensor reading of 200 is exceeded the heating operation is ceased. The value of n is set as 3. That is to say, once a difference in largest versus smallest readings of three times the initial background difference value (X) is exceeded, a 'fail test' message is given. For the purposes of exemplification, the sensor readings are expressed in nominal sensor reading units. In aspects, such readings may be correlated either directly or indirectly to temperature readings (e.g. expressed in ° C.).

| Test 1 (First four-clawed jewellery item) | | | | |
|---|---|---|---|---|
| | Sensor 1 | Sensor 2 | Sensor 3 | Sensor 4 |
| Initial reading | 20.2 | 20.1 | 20.4 | 20.0 |
| 1$^{st}$ reading | 23.4 | 23.3 | 23.2 | 23.1 |
| 2$^{nd}$ reading | 25.5 | 25.4 | 25.3 | 25.0 |
| . | . | . | . | . |
| . | . | . | . | . |
| Final reading | 220.4 | 220.1 | 220.4 | 220.0 |

In this test, the initial range of values is from 20.0 to 20.4 and the value of nX is therefore 3 times 0.4 (i.e. 1.2). It will be seen that throughout the test, the variation between highest and lowest recorded values is always <1.2, and the test therefore proceeds until sensor 1 records a value of 220.4 which corresponds to an overall sensor reading rise of greater than Y (i.e. 200) above the smallest start reading. This test indicates good integrity of the jewellery item, at each of its four claws.

| Test 2 (Second four-clawed jewellery item) | | | | |
|---|---|---|---|---|
| | Sensor 1 | Sensor 2 | Sensor 3 | Sensor 4 |
| Initial reading | 20.2 | 20.1 | 20.4 | 20.0 |
| 1$^{st}$ reading | 23.4 | 23.3 | 23.2 | 22.9 |
| 2$^{nd}$ reading | 25.5 | 25.4 | 25.3 | 24.8 |
| Final reading | 27.4 | 27.1 | 27.4 | 25.6 |

In this test, the initial range of values is from 20.0 to 20.4 and the value of nX is therefore 3 times 0.4 (i.e. 1.2). It will be seen that, the variation between highest and lowest recorded values is 0.5 for the 1$^{st}$ reading; 0.7 for the 2$^{nd}$ reading and then 1.8 for the third reading. Thus at the third reading point, the difference is >3X (i.e >1.2) and the test is stopped and a 'fail test' signal given. This test indicates poor integrity of the jewellery item as a whole and, in particular at its fourth claw.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

The invention claimed is:

1. A method for assessing the integrity of grip of a stone in a jewellery setting having plural gripping claws to grip said stone, the method comprising
heating the stone;
measuring conductive transfer of heat from the stone to each of said plural gripping claws; and
comparing said conductive heat transfer to said each gripping claw,
wherein a marked difference in conductive heat transfer to any of the gripping claws indicates a lack of integrity of grip.

2. A method according to claim 1, additionally comprising identifying which of the gripping claws has said marked difference in conductive heat transfer, thereby indicating lack of integrity of grip of any particular gripping claw.

3. A method according to claim 1, wherein said heating involves contacting the stone with a heater.

4. A method according to claim 3, wherein said heater is isolated from the gripping claws.

5. A method according to claim 1, wherein the heating is conducted for from one to ten seconds.

6. A method according to claim 1, wherein the temperature of each of the gripping claws is measured.

7. A method according to claim 6, wherein the temperature is measured by an electro thermometric method.

8. A method according to claim 7, wherein said electro thermometric method is selected from the group consisting of resistance thermometry, thermocouples, thermopiles, bolometers and semiconductor devices.

9. A method according to claim 1, wherein the conductive transfer of heat from the stone to each of said plural gripping claws is measured using an infra-red detection method.

10. A method according to claim 6, wherein the conductive heat transfer to said each gripping claw is compared by comparing the temperature measurements relevant to each claw.

11. A method according to claim 9, wherein the conductive heat transfer to said each gripping claw is compared visually using the display from an infra-red detector.

12. A method according to claim 1, wherein said marked difference is determined by electronically processing data relevant to the conductive heat transfer.

13. A method according to claim 1, additionally comprising signalling to indicate the presence of either positive or negative integrity for the setting as a whole.

14. A method according to claim 1, additionally comprising signalling to indicate whether any particular one of the gripping claws has positive or negative integrity of grip.

15. A method according to claim 13, wherein said signalling comprises providing an alert by emitting energy in a form selected from the group consisting of electromagnetic radiation, sound, electrical, kinetic and thermal energy.

16. A method according to claim 15, wherein the intensity of said alert is determined by the conductive heat transfer to the gripping claws.

17. Apparatus for use in assessing the integrity of grip of a stone in a jewellery setting having plural gripping claws to grip said stone, the apparatus comprising
a holder for holding said jewellery setting;
a heater for heating the stone; and
a heat transfer measure for measuring conductive transfer of heat from the stone to each of said plural gripping claws,
wherein a marked difference in conductive heat transfer to any of the gripping claws indicates a lack of integrity of grip.

18. Apparatus according to claim 17, wherein the apparatus additionally comprises a comparator for comparing said conductive heat transfer to said each gripping claw.

19. Apparatus according to claim 17, wherein the holder directly holds the jewellery setting.

20. Apparatus according to claim 17, wherein the jewellery setting forms part of an item of jewellery and the holder holds part of said item of jewellery.

21. Apparatus according to claim 17, wherein in use, the heater directly contacts the stone.

22. Apparatus according to claim 21, wherein in use, the heater is isolated from the gripping claws.

23. Apparatus according to claim 17, wherein the heater is moveable within the apparatus from a first position in which it does not contact the stone to a second position in which it contacts the stone for heating thereof.

24. Apparatus according to claim 17, wherein the heat transfer measure comprises a temperature sensor to measure the temperature of each gripping claw.

25. Apparatus according to claim 24, wherein the temperature sensor is an electro thermometer.

26. Apparatus according to claim 24, wherein the temperature sensor comprises a thermistor.

27. Apparatus according to claim 17, wherein the heat transfer measure comprises an infrared detector.

28. Apparatus according to claim 17, wherein the heat transfer measure comprises plural temperature sensors, each locating on a common sensor mounting.

29. Apparatus according to claim 28, wherein said plural temperature sensors locate on said common sensor mounting such that in use, each temperature sensor locates adjacent to one of the plural gripping claws of the jewellery setting.

30. Apparatus according to claim 28, wherein the common sensor mounting defines a generally concave surface and the plural temperature sensors are spaced at regular intervals on said concave surface.

31. Apparatus according to claim 28, wherein the sensor mounting is moveable within the apparatus from a non-contact position, in which the temperature sensors thereof are distant from the gripping claws of the jewellery setting to a contact position, in which in which each temperature sensor thereof contacts a gripping claw of the jewellery setting.

32. Apparatus according to claim 18, wherein the comparator comprises an electronic data processor for processing heat transfer measurement data.

33. Apparatus according to claim 17, wherein the apparatus includes an indicator to indicate the presence the presence of either positive or negative integrity for the setting as a whole.

34. Apparatus according to claim 17, wherein the apparatus includes an indicator to indicate whether any particular one of the gripping claws has positive or negative integrity of grip.

35. Apparatus according to claim 17, wherein the apparatus additionally comprises an alert for alerting when either the marked difference or an absence thereof is detected.

36. Apparatus according to claim 35, wherein the alert comprises an emitter for emitting energy in a form selected from the group consisting of electro-magnetic radiation, sound, electrical, kinetic and thermal energy.

37. Apparatus according to claim 36, wherein the emitter comprises a light emitting diode.

38. Apparatus according to claim 30, wherein the intensity of an alerting signal is coupled to the amount of heat transfer measured by the heat transfer measure.

39. Apparatus according to claim 17, for use in assessing the integrity of grip of a stone in a jewellery setting of a ring, said jewellery setting having plural gripping claws to grip said stone, the apparatus comprising
- a holder for holding said ring;
- a heater for heating the stone; and
- a heat transfer measure for measuring conductive transfer of heat from the stone to each of said plural gripping claws,
- wherein a marked difference in conductive heat transfer to any of the gripping claws indicates a lack of integrity of grip.

40. Apparatus according to claim 39 in the form of a box with a lid wherein the holder for the ring is comprised within the box;
- the heater is a contact heater located on the lid of the box; and
- the heat transfer measure comprises multiple temperature probes located within the box to contact the gripping claws when the ring is received by the holder.

41. Apparatus according to claim 40, wherein the box is configured such that the heater only contacts the stone when the lid of the box is closed.

* * * * *